ic acid feed

United States Patent [19]
Sinclair et al.

[11] Patent Number: 5,274,127
[45] Date of Patent: Dec. 28, 1993

[54] LACTIDE PRODUCTION FROM DEHYDRATION OF AQUEOUS LACTIC ACID FEED

[75] Inventors: Richard G. Sinclair; Richard A. Markle, both of Columbus; Russell K. Smith, Dublin, all of Ohio

[73] Assignee: BioPak Technology, Ltd., Golden, Colo.

[21] Appl. No.: 584,126

[22] Filed: Sep. 18, 1990

[51] Int. Cl.$^5$ .................. C07D 319/12; C07D 319/00
[52] U.S. Cl. ...................................... 549/274; 549/379
[58] Field of Search ............................ 549/379, 274

[56] References Cited

U.S. PATENT DOCUMENTS

| | | | |
|---|---|---|---|
| 1,095,205 | 5/1914 | Gruter et al. | 544/379 |
| 1,594,843 | 8/1926 | Lawrie | 544/379 |
| 1,995,970 | 3/1935 | Dorough | 260/2 |
| 2,163,268 | 6/1939 | Carothers et al. | 260/338 |
| 2,174,491 | 9/1939 | Watson | 260/67 |
| 2,189,572 | 2/1940 | Watson | 260/78 |
| 2,668,162 | 2/1954 | Lowe | 260/78.3 |
| 2,703,316 | 3/1955 | Schneider | 260/78.3 |
| 2,758,987 | 8/1956 | Salzberg | 260/78.3 |
| 2,768,973 | 10/1956 | Castle et al. | 260/602 |
| 3,322,719 | 5/1967 | Peilstöcker | 260/45.8 |
| 3,435,008 | 3/1969 | Schmitt et al. | 260/78.3 |
| 3,457,280 | 7/1969 | Schmitt et al. | 260/340.2 |
| 3,597,450 | 8/1971 | Schmitt et al. | 260/340.2 |
| 3,736,646 | 6/1973 | Schmitt et al. | 29/458 |
| 3,867,190 | 2/1975 | Schmitt et al. | 117/138.8 |
| 3,960,152 | 6/1976 | Augurt et al. | 128/335.5 |
| 4,033,938 | 7/1977 | Augurt et al. | 260/78.3 |
| 4,797,468 | 1/1989 | DeVries | 528/354 |
| 4,835,293 | 5/1989 | Bhatia | 549/274 |
| 4,990,222 | 2/1991 | Aigner et al. | 203/91 |
| 5,023,349 | 6/1991 | Bhatia | 549/274 |
| 5,023,350 | 6/1991 | Bhatia | 549/274 |
| 5,043,458 | 8/1991 | Bhatia | 549/274 |
| 5,053,485 | 10/1991 | Nieuwenhuis et al. | 528/354 |
| 5,053,522 | 10/1991 | Muller | 549/274.1 |
| 5,068,418 | 11/1991 | Kulprathipanja et al. | 562/580 |
| 5,075,115 | 12/1991 | Brine | 424/410 |
| 5,089,632 | 2/1992 | Paul | 549/274 |
| 5,091,544 | 2/1992 | Bhatia | 549/274 |

FOREIGN PATENT DOCUMENTS

| | | |
|---|---|---|
| 863673 | 2/1971 | Canada . |
| 0261572A1 | 3/1988 | European Pat. Off. . |
| 0264926A2 | 4/1988 | European Pat. Off. . |
| 221786 | 5/1910 | Fed. Rep. of Germany . |
| 267826 | 12/1913 | Fed. Rep. of Germany . |

(List continued on next page.)

OTHER PUBLICATIONS

Bezzi, "The Constitution of Some Polyglycolides", pp. 219–233, 1949, Gazz Chim. Ital. vol. 79.
Bezzi, "Transformation of Cyclic Esters Into Linear Polyesters", pp. 215–224, 1938; Gazz. Chim. Ital. vol. 68.

(List continued on next page.)

Primary Examiner—C. Warren Ivy
Assistant Examiner—Raymond Covington
Attorney, Agent, or Firm—Sheridan Ross & McIntosh

[57] ABSTRACT

The present invention is directed to a method for making L-lactide from aqueous L-lactic acid. Aqueous lactic acid feed for present purposes comprehends an aqueous mixture of one or more of $L_1A$, $L_2A$, and $L_3A$, optionally with LD being present. L-lactic acid is the preferred feed configuration for making L-lactide, and is to be understood even though the configuration symbol is not used throughout this application. Aqueous lactic acid feed is treated for removal of water therefrom until a degree of polymerization (DP) not substantially above about 2 is reached. The treatment then is ceased to produce a crude LD product. LD then is separated from the crude LD product. A preferred treatment involves heating the feed at elevated temperature to remove water. LD can be separated from the crude LD product by a variety of techniques to produce an LD-depleted product. This LD-depleted product, optionally augmented with additional aqueous lactic acid and/or water then can be readmitted to the process for making additional lactide. This cyclic or recycle process embodiment of the present invention enables very high lactide conversions to be realized.

13 Claims, No Drawings

FOREIGN PATENT DOCUMENTS

WO91/17155 11/1991 PCT Int'l Appl. .
WO92/00292 1/1992 PCT Int'l Appl. .
1007347 10/1965 United Kingdom .
1122229 7/1968 United Kingdom .
53074 5/1967 Fed. Rep. of Germany .
3632103A1 3/1988 Fed. Rep. of Germany .

OTHER PUBLICATIONS

Bezzi et al., "Dehydration Products of Lactic Acid Typifying the Transformation of Cyclic Esters into Linear Polyesters", 1936, Meeting of the Italian Academy of Science, Nov.

Bischoff et al., "Ueber Das Glycolid und Seine Homologen", pp. 262–265, 1893; Chem. Ber., vol. 26.

Carothers et al., "Studies of Polymerization and Ring Formation. X. The Reversible Polymerization of Six--Membered Cyclic Esters", pp. 761–771, (1932), J. Am. Chem. Soc., vol. 54.

Carothers, "Polymers and Polyfunctionality", pp. 39–53 (1936), Transactions of The Faraday Society, vol. 32.

Dietzel et al., "Über Das Chemische Gleichgewicht Zwischen Der Milchsäure und Ihren Anhydriden in Wässriger Lösung", pp. 1307–1314, (1925), Chem. Ber., vol. 58B.

Deibig et al., "I. Synthesis and Properties of Polytetramethyl Glycolide", pp. 123–131, (1971), Die Makromolekulare Chemie, vol. 145.

Deibig et al., "II. Thermal Behavior of Polytetramethyl Glycolide", pp. 133–139, (1971), Die Makromolekulare Chemie, vol. 145.

Filachione et al., "Lactic Acid Condensation Polymers: Preparation By Batch and Continuous Methods", pp. 223–228, (1944), Industrial and Engineering Chemistry, Mar., vol. 36, No. 3.

Hill et al., "Cyclic and Polymeric Formals", pp. 925–928, (1935), J. Am. Chem. Soc., vol. 57.

Holten, "Lactic Acid; Properties and Chemistry of Lactic Acid and Derivatives", pp. 221–231, (1971), Verlag Chemie.

Imasaka et al., "Synthesis of Degradable Terpolymers Responding to External Stimuli Such as Ph, Ionic Strength, and Temperature", pp. 715–722, (1991), Makromol. Chem. vol. 192.

Ikada et al., "Stereocomplex Formation Between Enantiomeric Poly(Lactides)", pp. 904–906, (1987), American Chemical Society, Macromolecules, 20.

Jackanicz et al., "Polylactic Acid as a Biodegradable Carrier for Contraceptive Steroids", pp. 227–234, (1973), The Population Counsel, Sep., vol. 8, No. 3.

Jungfleisch et al., "Organic Chemistry—of Lactyllactyllactic Acid and the Dilactide of Racemic Lactic Acid", pp. 502–505, (1905), Academie Des Sciences, Meeting of Feb. 20.

Jungfleisch et al., "Organic Chemistry—on The Dilactide of the Right", pp. 111–113, (1905) Academie Des Sciences, Meeting of Jul. 10.

Jungfleisch et al., "Organic Chemistry—on the Dilactide of Left Lactic Acid", pp. 637–639, (1906), Academie Des Sciences, Meeting of Mar. 12.

Jungfleisch et al., "Organic Chemistry—on Ethyl Lactyllactate", (1907), Academie Des Sciences, Meeting of Feb. 25.

Jungfleisch et al., "Organic Chemistry—on Inactive Dilactylic Acid", p. 979, (1907), Academie Des Sciences, Meeting of May 6.

Kleine et al., "High Molecular Weight, Especially Optically Active Polyesters of Lactic Acid: An Investigation of the Stereochemistry of Macromolecular Compounds", pp. 1–21, (1958), Report from the Research laboratory for Macromolecular Chemistry, Dec.

Kulkarni et al., "Polylactic Acid for Surgical Implants", pp. 839–843, (1966), Arch. Surg., vol. 93, Nov.

Light, "Lactic Acid Resins", pp. 135–136, (1940), Paint Manufacture, Jun.

Montgomery, "Acidic Constituents of Lactic Acid-Water Systems", pp. 1466–1468, (1952), J. Am. Chem. Soc., vol. 74.

Watson, "Composition of Lactic Acid, Production of a Highly Concentrated Acid", pp. 399–401, (1940), Industrial and Engineering Chemistry, vol. 32, No. 3.

Wise, "Biopolymeric Controlled Release Systems", pp. 3–28, (1984), CRC Press, vol. 1.

Wise, "Biopolymeric Controlled Release Systems", pp. 187–199, (1984), CRC Press, vol. 2.

Wise, et al., "Lactic/Glycolic Acid Polymers", pp. 237–270, Dynatech R/D Company, Cambridge, Mass., U.S.A. (1984).

Wislicenus, "On the Optically Active Lactic Acid of Sarcolactic Liquid, the Paralactic Acid", pp. 318–319, (1873), Liebigs Ann. Chem. vol. 167.

LACTIDE PRODUCTION FROM DEHYDRATION OF AQUEOUS LACTIC ACID FEED

BACKGROUND OF THE INVENTION

The present invention relates to the catalytic production of lactide and more particularly to its direct production from lactic acid.

For purposes of this application, the following definitions apply:

$L_1A$: lactic acid or 2-hydroxypropionic acid
LD: lactide or 3,6-dimethyl-1,4-dioxane-2,5-dione
$L_2A$: lactoyllactic acid or lactic acid dimer
$L_3A$: lactoyllactoyllactic acid or lactic acid trimer
$L_nA$: n-oligomer of lactic acid.

The DP or degree of polymerization of lactic acid is "n".

Lactic acid has one asymmetric carbon atom and, thus, can be found in two enantiomeric forms. Lactide, on the other hand, has two asymmetric carbon atoms so that it can be found in three steroisomeric forms: L-lactide in which both asymmetric carbon atoms possess the L (or S) configuration; D-lactide in which both asymmetric carbon atoms possess the D (or R) configuration; and meso-lactide in which one asymmetric atom has the L configuration and the other has the D configuration. L-lactide and D-lactide are enantiomers while D,L-lactide is the meso species. In the production of lactide from lactic acid, it would be advantageous if the absolute configuration of the lactic acid feed was maintained in its conversion to lactide. Enantiomeric lactide, especially L-lactide, has utility in the production of polymers, especially in the production of environmentally degradable polymers such as proposed in commonly-assigned U.S. applications Ser. Nos. 387,670; 387,676; 387,678; and 386,844.

Heretofore, production of lactide from lactic acid has proceeded by the initial formation of oligomeric lactic acid, $L_nA$, such as by dehydration of aqueous lactic acid, followed by a catalytic transesterification reaction known as "back-biting" as illustrated below:

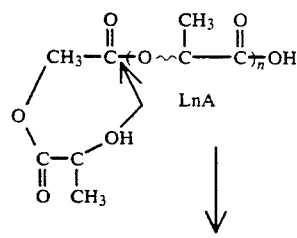

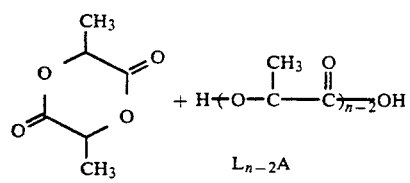

As illustrated above, back-biting depolymerization of $L_nA$ results in the production of lactide. Catalysts proposed for such a reaction include tin powder, tin halides, or tin carboxylates (EP Publication 261,572); tin alkoxides (U.K. Pat. No. 1,007,347); and zinc or tin (EP Publication 264,926).

Direct conversion of lactic acid into lactide with or without preservation of absolute configuration of asymmetric atoms is not shown in the art.

BROAD STATEMENT OF THE INVENTION

The present invention is directed to a method for making L-lactide from aqueous L-lactic acid. Aqueous lactic acid feed for present purposes comprehends an aqueous mixture of one or more of $L_1A$, $L_2A$, and $L_3A$, optionally with LD being present. L-lactic acid is the preferred feed configuration for making L-lactide, and is to be understood even though the configuration symbol is not used throughout this application. Aqueous lactic acid feed is treated for removal of water therefrom until a degree of polymerization (DP) not substantially above about 2 is reached. The treatment then is ceased to produce a crude LD product. LD then is separated from the crude LD product. A preferred treatment involves heating the feed at elevated temperature to remove water during which additional LD forms.

LD can be separated from the crude LD product by a variety of techniques to produce an LD-depleted product. This LD-depleted product, optionally augmented with additional aqueous lactic acid and/or water then can be readmitted to the process for making additional lactide. This cyclic or recycle process embodiment of the present invention enables very high lactide conversions to be realized.

Advantages of the present invention include the ability to convert lactic acid directly into lactide of high purity. Another advantage is that the asymmetric carbon atoms in the product lactide predominate in the same absolute configuration as the feed lactic acid from which it was made. Another advantage is a process which is amenable to recycling unreacted lactic acid and by-products formed during the treatment process. The simplicity of the process is yet a further advantage. These and other advantages will be readily apparent to those skilled in the art based upon the disclosure contained herein.

DETAILED DESCRIPTION OF THE INVENTION

The lactic acid feed is in aqueous form for conversion to its vapor phase as an initial step of the process of the present invention. The role played by water in the process can be appreciated by reference to the following equilibrium reactions:

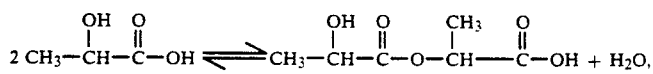

or written another way:

etc.

Thus, it will be observed that $L_1A$ is in equilibrium with higher oligomers of lactic acid and water. By removing water, these reactions shift to the right. In fact, $L_2A$ and higher lactic acid oligomers ($L_nA$) are made by dehydrating aqueous lactic acid. Sufficient water, then, should be present so that the equilibrium detailed above favors the presence of $L_1A$ and $L_2A$ in as the feedstock. Extra quantities of water in the feedstock are permissible at the expense of the handling and energy costs associated therewith.

What was unknown in the foregoing equilibrium reactions is that when water is removed so that higher DP oligomeric lactic acid is produced, LD also is produced. As the data will demonstrate, at a DP of about 2, the LD content of the material is maximized. It is worth restating that removal of water is the driving force behind this reaction. If water removal is ceased at a DP of about 2, LD then can be separated from the reaction mixture and recovered for use. It will be recognized that the art has always dehydrated aqueous lactic acid to form oligomeric $L_nA$ having a DP of 5 or above. The art then employed a catalyzed reaction known as back-biting for production of lactide. What the art failed to grasp was that lactide formed during the dehydration and its content was maximized at about 2. Also, it was unrecognized that LD is sufficiently stabe in the presence of hot $L_nA$ and water to be isolated in significant quantities.

Since the crude LD product has a DP of around 2 and the process modality involves removal of water, the appropriate lactic acid feed is enriched in $L_1A$ and $L_2A$, and depleted in higher oligomeric $L_nA$ species. That is not to say that $L_3A$, $L_4A$, and some higher olgomeric $L_nA$ species are not present in the lactic acid feed, but their presence should be minimized in order to maximize LD production in accordance with the precepts of the present invention. Lactic acid feedstocks enriched in higher oligomeric $L_nA$ species preferably should be hydrolyzed in order to take advantage of the equilibrium equations detailed above for enriching the lactic acid feed in $L_1A$ and $L_2A$. The presence of higher oligomeric $L_nA$ species, then, only serves to compromise yields of LD by the present process. The lactic acid feedstock can contain LD it self, especially when employing a recycle of the crude LD feedstock that has been treated for separating LD product therefrom. The presence of LD in the feedstock appears to have no adverse consequences on conversion of $L_1A$ and $L_2A$ to LD, i.e. LD can be achieved by kinetic means rather than relying strictly on equilibrium amounts.

A variety of reactors and reaction schemes can be envisioned for treating the aqueous lactic acid feed for removal of water. A straightforward treatment involves subjecting the aqueous lactic acid to heating at elevated temperature (e.g. 150°-225° C.) to remove water therefrom until the heated feed has a DP not substantially above about 2. Alternative treatment schemes can be envisioned for removal of water, however. An additional treatment may include the addition of a water-getter which preferentially reacts with water for forming a compound that is innocuous in the process. Such compounds include, for example, anhydrides (e.g. acetic anhydride), acetals (e.g., the diethyl acetal of acetaldehyde), carbodiimides, and ketals (e.g. dimethyl ketal of acetone). Yet another technique that can be envisioned for removing water from the aqueous lactic acid feed involves subjecting feed to an osmotic membrane suitable for permitting water molecules to pass therethrough, yet having the ability to exclude $L_1A$, $L_2A$, LD, and the like. So long as water is preferentially removed from the aqueous lactic acid fee until a DP not substantially above about 2 is reached, the equilibrium reactions detailed above result in formation of LD product.

In a non-catalyzed process, it is believed that $L_2A$ cyclizes (or esterifies) to form LD. LD is in equilibrium with $L_2A$ in the reaction mixture, however, the crude LD product produced is not an equilibrium reaction mixture. That is, it appears that LD is formed during the treatment to raise the DP to a value not substantially above about 2. The treatment then must cease and the crude LD product subjected to processing for LD removal. If the crude LD product reaction mixture is permitted to stand for too long, the reactants and products in the reaction mixture will equilibrate and likely some LD values will return to $L_2A$ or react to form $L_3A$ and $L_4A$. Extended periods of time between generation of the crude LD product and separation of LD therefrom is not recommended.

Conventional back-biting or depolymerization reactions of higher oligomeric $L_nA$ species for LD production are conducted in the presence of catalysts. Accordingly, research endeavors in connection with the present invention also explored the effect of catalysts on the present process. As the data in the examples will reveal, the presence of conventional catalysts, e.g. tin compounds, had very little effect on LD production compared to conducting the process in substantial absence of such catalysts. These results may be explained by postulating the tin catalyst functionality to involving cleaving higher DP oligomeric $L_nA$ species into smaller fragments that form lactide. At a DP of around 2, the mechanism for LD production is believed to primarily involve a rapid ring closure that does not require the presence of a catalyst. Thus, the presence of conventional LD-yielding catalysts are unnecessary in the present process, though their presence is not excluded.

A variety of separation techniques also can be envisioned for separating LD from crude LD product produced by the treatment of the aqueous lactic acid feed. These techniques include, for example, cold water washing of the crude LD product, fractional distillation of the crude LD product, solvent extraction of the crude LD product, and recrystallization of the crude LD product, for LD recovery therefrom. Combinations of these techniques may be used additionally.

The presently preferred LD recovery processing scheme involves distillation which preferably is conducted under vacuum and/or utilizing a codistillation organic solvent to facilitate removal of LD from the crude LD product. A codistillation solvent is convenient, particularly for large stills, where heat for LD formation and distillation requires a reboiler. The codistillation solvent provides heat to the upper part of the still and provides heat transfer for the reaction. Additionally, a codistillation solvent dilutes the vapor from the feed and enhances the ring closure process. Particularly convenient is the use of a codistillation solvent that is immiscible with LD and $L_nA$ species. This provides additional vapor pressures of the solvent and LD, and separation of LD from the solvent. One class of codistillation solvents meeting the preferred requirements comprise alkyl benzenes, especially those with a boiling point equal to or slightly higher than that of LD. Representative preferred alkyl benzene solvents include higher alkyl benzenes including $C_{10}$–$C_{22}$ alkyl benzenes, and preferably dodecyl benzene or tridecyl benzene. Distillation cuts that have an average composition of dodecyl benzene also are quite appropriate for use in the present invention. These mixed cuts supply the necessary boiling point, are non-toxic, and are commercially available.

The crude LD product which has been treated for removal of LD contains $L_nA$ values that can be converted into LD typically by treating the product residue for its enrichment in $L_1A$ and $L_2A$. When distillation is the water removal treatment of choice, the still bottoms additionally can be combined with the product residue for re-admission to the process. Hydrolyzing this recycle stream for its enrichment in $L_1A$ and $L_2A$ typically is recommended most often with augmentation with additional fresh aqueous lactic acid feed. Overall LD yields exceeding 90% can be expected when employing such recycle techniques.

The following examples show how the present invention has been practiced, but should not be construed as limiting. In this application, all percentages and proportions are by weight and all units are in the metric system, unless otherwise expressly indicated. Also, all citations referred to herein are incorporated expressly herein by reference.

EXAMPLES

Example 1

A three-neck, one-liter round-bottom flask was fitted with a mechanical stirrer, nitrogen sparged, and a straight distillation take-off to a condenser, and the receiver to a vacuum take-off and manometer. The flask was charged with 650 ml (770.4 g) of 88% L-lactic acid feed and heated at 120°–130° C. with stirring and nitrogen bubbling. Water was distilled using a water aspirator at 150–200 Torr. Aliquots are removed during the course of the heating and characterized by titration for DP (degree of polymerization). Then, after methylation with diazomethane, the aliquots were characterized by gas chromatography (GC) for percentages of $L_2A$, $L_3A$, $L_4A$, and LD. The results recorded are set forth below.

TABLE 1

| $DP^{(a)}$ Conditions of OLA Pressure | Composition (wt %)$^{(b)}$ | | | | | Distillation Temperature | |
|---|---|---|---|---|---|---|---|
| | $L_1A$ | $L_2A$ | $L_3A$ | $L_4A$ | LD | (°C.) | (torr) |
| 1.29$^{(c)}$ | 75.4 | 20.1 | 3.3 | 0.3 | 1.3 | — | — |
| 1.44 | 49.0 | 28.5 | 11.5 | 2.2 | 3.3 | 120–130 | 400–210 |
| 1.59 | 27.8 | 27.8 | 20.2 | 10.3 | 8.6 | 150 | 90 |
| 1.99 | 11.8 | 16.7 | 14.4 | 8.8 | 18.4 | 155 | 153 |
| 2.01 | 12.3 | 14.0 | 13.8 | 9.8 | 19.0 | 160 | 85 |
| 2.07 | 8.3 | 6.0 | 15.0 | 15.0 | 27.9 | 175 | 30 |
| 2.63 | 2.1 | 0.7 | 1.0 | 0.8 | 14.7 | 185$^{(d)}$ | 30$^{(d)}$ |
| 24.0 | 0.4 | 1.4 | 0.6 | 0.4 | 11.5 | 185$^{(d)}$ | 10$^{(d)}$ |

$^{(a)}$Titration with KOH. OLA is oligomeric lactic acid.
$^{(b)}$Gas chromatography of methyl esters.
$^{(c)}$L-lactic acid feed.
$^{(d)}$Prolonged (overnight) distillation.

As the above-tabulated data reveals, LD production surprisingly peaked at a DP of about 2. This peak LD production was achieved under relatively mild distillation conditions in a facile manner. If the flask contents are further dehydrated to higher DPs, LD eventually will begin to distill. Continued distillation to steady state results in LD in the pot being approximately 3–6% of the oligomeric lactic acids present, i.e. in the conventional back-biting mode.

Examples 2–11

A pot was connected to a distillation head and cooled receiver, feed funnel, and manistat for maintaining a pressure of about 50–60 torr. Aliquots of the various DP materials of Example 1 were incrementally distilled by adding them dropwise from the heated funnel (145° C.) to the pot under rapid stirring. The pot temperature of the melt was monitored by an internal thermocouple and the pot was heated by an external oil bath. The pot temperature was varied and the distillation rates noted. The amount of material that distills rapidly, i.e. several drops per second, was weighed and compared to the amount remaining in the pot. The distillations generally were marked by rapid distillations at the beginning of each run, slowing eventually to approximately 1/5 the initial rate, i.e. 1 drop per 2–3 seconds. The results are recorded in the following tables.

TABLE 2

| Example | $DP^{(a)}$ | Amount$^{(b)}$ Distilled/ Not Distilled (wt %) | Distillation$^{(c)}$ Temperature (°C.) | Distillation Rate |
|---|---|---|---|---|
| 2 | 1.29 | 67/16 | 200 | rapid |
| 3 | 1.44 | 49/42 | 193 | rapid |
| 4 | 1.59 | 39/58 | 220 | rapid |
| 5 | 1.99 | 52/48 | 197 | slow |
| 6 | 1.99 | 54/46 | 225 | rapid |
| 7 | 1.99 | 43/65 | 215 | slow |
| 8 | 2.07 | 15/76 | 202 | moderate |
| 9 | 2.63 | trace distilled | 204 | very slow |
| 10 | 2.63 | 8/85 | 227 | very slow |
| 11 | 24.0 | trace distilled | 204 | very slow |

$^{(a)}$By titration.
$^{(b)}$As weight percent of starting material.
$^{(c)}$50–60 torr.

TABLE 3

| Example | $DP^{(a)}$ | L-LD$^{(b)}$ (wt %) | | |
|---|---|---|---|---|
| | | Starting Material | Distillate | Pot |
| 2 | 1.29 | 1.3 | 1.1 | 18.5 |
| 3 | 1.44 | 3.3 | 1.4 | 25.5 |
| 4 | 1.59 | 8.6 | 18.8 | 26.1 |
| 6 | 1.99 | 18.4 | 43.5 | 13.2 |
| 8 | 2.07 | 27.9 | 35.2 | 24.7 |
| 9 | 2.63 | 14.7 | 12.7 | 7.1 |
| 11 | 24 | 11.5 | trace | 5.8 |

$^{(a)}$Degree of polymerization of starting material, by titration.
$^{(b)}$Composition of GC analyses after methylation with diazomethane.

The results depicted at Table 2 show that progressively higher temperatures are required to distill LD as the DP and melt viscosity increase. The amount of material that distills rapidly increases at lower DP, however, the best yield and purity are found at approximately a DP of 2. This is seen by comparing the data of Table 2 to that of Table 3 where the products were assayed. These examples demonstrate that LD can be distilled rapidly from lower DP materials and that this rate is much faster than the prior art cracking mechanism at higher DPs, viz. DPs of 5 and above. The best enrichment of LD occurs at approximately a DP of 2 where it also distills rapidly. Since the amount of LD after distillation exceeds the amount of LD before distillation, LD is formed during distillation, probably by a ring-closure mechanism.

EXAMPLES 12–14

The runs of Examples 8, 10, and 11 were repeated, except that one wt-% stannous octoate was added to the starting material. The results recorded are set forth below.

TABLE 4

| Example | DP[a] | Catalyst,[b] With/Without | Distilled[c] (wt %) | Distillation Rate |
|---|---|---|---|---|
| 8 | 2.07 | without | 15 | rapid |
| 12 | 2.07 | with | 17 | rapid |
| 10 | 2.63 | without | 8 | very slow |
| 13 | 2.63 | with | 48 | moderate |
| 11 | 24 | without | trace | very slow |
| 14 | 24 | with | 5 | very slow |

[a]By titration
[b]One (1) percent stannous octoate
[c]As weight percent of starting material.

The rate of distillation of lactide was accelerated by use of the catalyst only when the DP was greater than 2 according to the above-tabulated data. This is understandable in terms of the probable chemical mechanisms involved. Stannous octoate is believed to operate by cleaving higher DP oligomeric lactic acids into smaller fragments that form lactide and is, therefore, effective in this DP regime. At a DP of about 2, the mechanism probably primarily is a rapid ring closure without catalyst, which has little discernable effect on distillation rates at this DP. Accordingly, conventional catalysts are superfluous to the inventive lactide production process.

Example 15

A bench apparatus was used to demonstrate a unit operation for the continuous addition of a DP 2 oligomeric lactic acid feed to a distillation column for forming, distilling, and purifying product LD. The column heat was supplied by reboiler fluid that refluxes up to a 5-plate Oldershaw column. The feed was fed to the top of the column where LD codistills with the reboiler vapor. Further LD forms as the feed percolates down through the column. Higher $L_nA$ oligomers (n greater than 3) eventually find their way to the still bottom. Water is removed through a hot condenser which rejects any lactic acid, returning the latter to the column. LD is distilled through a lower side port to a cooled fraction collector.

The reboiler fluid used was an alkyl benzene (AB) where the alkyl moeity is a mixture of $C_{11}$-$C_{14}$ isomers. The alkyl benzene had a boiling range of 220°-230° C. at 56 torr after a small forecut was taken off. The alkyl benzene is totally immiscible hot or cold, with LD or $L_nA$. the heat flux was maintained such that the alkyl benzene feebly distilled as the feed is added dropwise at a rate of approximately 17-75 g/hr. Approximately 3-4 wt-parts of crude LD distill per 1 wt-part of alkyl benzene. Alkyl benzene alone distills at 215°-220° C. at 58 torr, whereas as under the same conditions LD distills at 189° C. Alkyl benzene and lactide codistill at 165°-177° C. at 56 torr. The feed DP2 material was heated to approximately 80°-120° C. and delivered via a small teflon tube to the system. The feed is pulled into the system by vacuum or by pumping using a peristaltic pump. The rate was governed by the temperature of the feed, its viscosity, and the interior diameter of the tube, or the speed of the pump, whichever was used.

Lactic acid feed of DP2 (146.22 g) was fed to the column over a 2 hour period. The reboiler was held at a temperature of 222°-224° C. and a pressure of 94 torr. The top plate in the column was held at about 174°-178° C., the LD take-off point was at a temperate of about 167° C., the supply pot of feed was held at about 80°-90° C., and the teflon feedline was held at a temperature of 44° C. and the pressure controlled at 94 torr, throughout the column using manostats, manometers, cold traps, and vacuum pumps. After 2 hours, the pressure was lowered to 53 torr and an additional 51.82 g of feed material was fed to the column over a 95 minute time period. The products were collected from the two pressure conditions in separate fractions.

The first, higher-pressure fraction yielded 66.05 g of distillate, from which alkyl benzene solvent was decanted. The lower phase from the decantation procedure yielded a crude white crystalline LD product which was washed with low-boiling petroleum ether and vacuum dried to obtain 49.53 g of LD product. In a similar fashion, the second, lower-pressure cut yielded 62.45 g of distillate and 50.48 g of crude LD after washing with petroleum ether to remove the alkyl benzene solvent. The still-bottoms were cooled and alkyl benzene decanted to obtain 94.33 g of oligomeric lactic acids. The water condenser removed 4.8 ml of water. The material balance was calculated at 100.6%.

Crude lactide yield was based on conversion of $L_2A$ to LD at 88.9% of theoretical. On this basis, the overall yield of crude LD was 56.8%. GC assays of the two cuts were performed after treating an aliquot with diazomethane and comparing to standards. The GC analysis is set forth below.

TABLE 4

| Component | GC Assay (wt %) | |
|---|---|---|
| | Cut 1 | Cut 2 |
| LA | 36.3 | 19.0 |
| $L_2A$ | 8.0 | 4.6 |
| LD | 46.2 | 73.1 |
| $L_3A$ | 0 | 0 (<0.5) |
| AB | 3.4 | 1.2 |
| Total | 93.9 | 97.9 |

The overall yield of LD before purification was calculated at 34.6%. These results demonstrate that the crude LD product of DP 2 can be subjected to continuous codistillation with an appropriate solvent for collecting LD product.

Example 16

The procedure of Example 15 was repeated, except that 116.87 g of DP 2.13 feed was fed over 3.0 hours at a constant pressure of 53 torr. The crude LD collected after washing and drying weighed 73.43 g. After the addition was stopped, a second cut was taken since the distillation was continued for another 1.0 hr. The second cut provided 14.83 g of crude LD after washing and drying. The first cut, during the continuous addition, calculates as 70.7% of theory, neglecting impurities, and the second cut calculates as 14.3% of theory. A material balance of 103% was found for the LA and alkyl benzene materials. The two cuts were assayed by GC with the following results:

TABLE 5

| Component | GC Assay (wt %) | |
|---|---|---|
| | Cut 1 | Cut 2 |
| $L_1A$ | 15.0 | 0 |
| $L_2A$ | 5.7 | 3.6 |
| LD | 63.5 | 78.7 |
| $L_3A$ | 0. | 0 |
| AB | 3.8 | 3.4 |
| $H_2O$ | 0.85 | 0.90 |

TABLE 5-continued

| Component | GC Assay (wt %) | |
|---|---|---|
| | Cut 1 | Cut 2 |
| Total | 8.88 | 86.6 |

Finally, the still bottom assay revealed the presence of 2.9% LD and 0% for $L_1A$, $L_2A$, and $L_3A$.

Example 17

The LD from the first cut of Example 16 was recrystalized in dry methyl isobutyl ketone (MIBK), the LD separated by filtration, and the MIBK filtrate stripped on a rotary evaporator. The filtrate residue was combined with the still bottom from Example 16 by mixing and heating briefly at 120°–140° C. The DP of this mixture, by titration, was 2.37. The mixture was reconstituted to a DP of about 2.0–2.1 by mixing 2.96 ml of hot feed lactic acid (85% L-lactic acid). This reconstituted mixture assayed by GC to be 5.1% $L_1A$, 4.9% $L_2A$, and 35.4% LD. The balance of the material probably was higher oligomers, $L_nA$ (n greater than 3).

The reconstituted material was recycled in the procedure set forth in Example 16. The feed weighed 94.19 g. The product recovered after the process was washed and dried to yield 44.34 g of a crude, white crystalline LD, which assayed at 65–71% LD. This experiment demonstrates the ability to recycle still bottoms to produce additional product LD.

Examples 18–19

The still bottoms and purification rejects from Example 17 were reconstituted with additional 85% $L_1A$ to a DP of 2.0–2.1, and reused in a second recycle. In a similar manner, a third recycle was performed at the end of the second recycle using its still bottoms and purification rejects. The results recorded are set forth below.

TABLE 6

| Example | Recycle | Crude LD,[a] percent of theory | GC Assay, weight percent | LD Yield/Cycle,[b] percent of theory |
|---|---|---|---|---|
| 16 | 9 | 70.7 | 65.8 | 46.5 |
| 17 | 1 | 52.9 | 71.0 | 37.5 |
| 18 | 2 | 63.7 | 76.4 | 48.7 |
| 19 | 3 | 68.3 | 66.2 | 45.2 |
| Avg. | | 62.5 | 70.5 | 43.9 |

[a][Weight of crude distillate/weight of starting material × 0.889] × 100.
[b]Obtained by multiplying column 2 (crude LD) by column 3 (assay).

TABLE 7

| Example | Component (wt %) | | | | | |
|---|---|---|---|---|---|---|
| | $L_1A$ | $L_2A$ | LD | $L_3A$ | AB | GC Total |
| 16 | 15.0 | 5.7 | 65.8 | 0 | 3.8 | 89.6 |
| 17 | 13.0 | 5.5 | 71.0 | 0 | trace | 89.5 |
| 18 | 12.0 | 5.0 | 76.4 | 0 | 1.5 | 94.9 |
| 19 | 21.0 | 4.0 | 66.2 | trace | 2.1 | 93.3 |

The above-tabulated results demonstrate that the inventive process can be conducted in a continuous recycle manner with substantially no drop in LD yield and no apparent loss of material. The process when run continuously should provide LD yields exceeding 90%.

We claim:

1. A method for making lactide from aqueous lactic acid feed enriched in $L_1A$ and $L_2A$, which comprises:
    treating said feed to remove water therefrom until the treated feed has a DP not substantially above about 2 as measured by titration, and then ceasing said treating to make a crude LD product; and
    separating LD from said crude LD product.

2. The method of claim 1 wherein said treating is selected from the group consisting of heating at elevated temperature, addition of a water-getter which preferentially reacts with water, and using an osmotic membrane.

3. The method of claim 2 wherein said water getter is one or more of an anhydride or a ketal.

4. The method of claim 1 wherein said separating is by one or more of cold water washing, fractional distillation, solvent extraction, and solvent recrystallization.

5. The method of claim 4 wherein said separation technique is by distillation.

6. The method of claim 5 wherein said distillation is conducted utilizing a codistillation organic solvent.

7. The method of claim 6 wherein said codistillation solvent comprises an alkyl benzene.

8. The method of claim 7 wherein said alkyl benzene is selected from the group consisting of dodecyl benzene, tridecyl benzene, and mixtures thereof.

9. The method of claim 1 wherein the crude LD product from which LD has been separated is reconstituted to have a DP of less than 2 and recycled for additional treating.

10. A method for making lactide from aqueous lactic acid feed enriched in $L_1A$ and $L_2A$, and depleted in higher oligomeric $L_nA$ species, which comprises:
    subjecting said feed to heating at elevated temperature to remove water therefrom until the heated feed has a DP not substantially above about 2, and then ceasing said heating to produce a crude LD product; and
    separating LD from said crude LD product.

11. The method of claim 10 wherein said heating is conducted under vacuum.

12. The method of claim 10 wherein said heating is at a temperature ranging from about 150°–225° C.

13. The method of claim 10 wherein the crude LD product from which LD has been separated is reconstituted to have a DP of less than 2 and recycled for additional treating.

* * * * *